(12) United States Patent
Noyes et al.

(10) Patent No.: US 12,357,571 B2
(45) Date of Patent: Jul. 15, 2025

(54) LOADING OF EXTRACELLULAR VESICLES THROUGH IMPARTING OF MECHANICAL SHEAR

(71) Applicant: LONZA SALES AG, Basel (CH)

(72) Inventors: Aaron R. Noyes, Melrose, MA (US); Michael P. Mercaldi, Wilmington, MA (US); Kathryn E. Golden, Braintree, MA (US); Raymond W. Bourdeau, Watertown, MA (US); Michael F. Doherty, Somerville, MA (US); Konstantin Konstantinov, Waban, MA (US); Douglas E. Williams, Boston, MA (US)

(73) Assignee: LONZA SALES AG, Basel (CH)

( * ) Notice: Subject to any disclaimer, the term of this patent is extended or adjusted under 35 U.S.C. 154(b) by 0 days.

(21) Appl. No.: 18/045,727

(22) Filed: Oct. 11, 2022

(65) Prior Publication Data

US 2023/0301917 A1    Sep. 28, 2023

Related U.S. Application Data

(63) Continuation of application No. 17/014,961, filed on Sep. 8, 2020, now abandoned, which is a continuation of application No. 16/190,058, filed on Nov. 13, 2018, now abandoned.

(60) Provisional application No. 62/588,143, filed on Nov. 17, 2017.

(51) Int. Cl.
*A61K 9/1278*   (2025.01)
*A61K 9/1275*   (2025.01)
*C12N 15/11*    (2006.01)
*C12N 15/113*   (2010.01)

(52) U.S. Cl.
CPC .......... *A61K 9/1278* (2013.01); *A61K 9/1275* (2013.01); *C12N 15/111* (2013.01); *C12N 15/113* (2013.01); *C12N 2310/14* (2013.01); *C12N 2310/3515* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 7,939,562 | B2 | 5/2011 | Grinberg et al. |
| 9,629,929 | B2 | 4/2017 | Lötvall et al. |
| 9,858,477 | B2 | 1/2018 | Nakamura et al. |
| 11,261,465 | B2 | 1/2022 | Tandon et al. |
| 2008/0268542 | A1 | 10/2008 | Rubio et al. |
| 2016/0074507 | A1 | 3/2016 | Manel et al. |
| 2017/0340563 | A1 | 11/2017 | Javeri et al. |
| 2019/0175506 | A1 | 6/2019 | Noyes et al. |

FOREIGN PATENT DOCUMENTS

| | | |
|---|---|---|
| WO | 2000/054057 A1 | 9/2000 |
| WO | 2013/059343 A1 | 4/2013 |
| WO | 2013/070324 A1 | 5/2013 |
| WO | 2016/077639 A2 | 5/2016 |
| WO | 2016/168680 A1 | 10/2016 |
| WO | 2017/004526 A1 | 1/2017 |
| WO | 2017/161010 A1 | 9/2017 |

OTHER PUBLICATIONS

Jo et al. Nanoscale, 2014, 6, 12056-12064.*
Su, Yang. Microfluidics. Creating Nanoparticles with Microfluidizer High-Shear fluid Technology available on Jan. 11, 2017 at https://static.horiba.com/fileadmin/Horiba/Products/Scientific/Particle_Characterization/Webinars/Slides/TE027.pdf retrieved on Mar. 27, 2023, 43 pages.*
O'dea et al. PLoS One. 2017; 12(3): e0174779 Mar. 30, 2017.*
How do you convert from %w/v to molarity retrieved from https://How do you convert from %"w/v" to molarity? + Example (socratic.org) retrieved Jul. 10, 2024.*
"C12H22O11 (Sucrose) Molar Mass" retrieved from ttps://www.chemicalaid.com/tools/molarmass.php?formula=C12H22O11&hl=en retrieved Jul. 10, 2024.*
Ambardekar et al. Biomaterials. Feb. 2011; 32(5): 1404-141.*
Bosch et al., "Trehalose prevents aggregation of exosomes and cryodamage," Science Report 6: 36162 (2016).
Burdette et al., "STING is a direct innate immune sensor of cyclic di-GMP," Nature 478(7370):515-518 (2012).
Jo et al., "Large-scale generation of cell-derived nanovesicles," Nanoscale 6(20): 12056-12064 (2014).
Kamerkar et al., "Exosomes facilitate therapeutic targeting of oncogenic Kras in pancreatic cancer," Nature 546(7659):498-503 (2017).
Li et al., "Hydrolysis of 2'3'-cGAMP by ENPPI and design of nonhydrolyzable analogs," Nature Chemical Biology 10(12):1043-1048 (2014).
M-110EH-30 Microfluidizer™ Processor, Microfluidics (2012), accessed at chrome-extension://efaidnbmnnnibpcajpcglclefindmkaj/https://wolfson.huji.ac.il/purification/pictures/Microfluidics_microfluidizer_modelM110EHIS%29.pdf on May 1, 2020, 2 pages.
Martineau et al., "Expression of an antibody fragment at high levels in the NPL6 bacterial cytoplasm," Journal of Molecular Biology 280(1):117-127 (1998).
Miryabe et al., "A new adjuvant delivery system 'cyclic di-GMP/YSK05 liposome' for cancer immunotherapy," Journal of Controlled Release 184: 20-27 (2014).
"Recipe: Phosphate Buffered Saline," (2006) Cold Spring Harbor Protocols, accessed at http://cshprotocols.cshlp.org/content/2006/1/pdb.rec8247 on Dec. 4, 2019, 1 page.
Sharei et al., "A vector-free microfluidic platform for intracellular delivery," Proc Natl Acad Sci USA 110(6):2082-2087 (2013).

(Continued)

*Primary Examiner* — Oluwatosin A Ogunbiyi
(74) *Attorney, Agent, or Firm* — MEDLER FERRO WOODHOUSE & MILLS PLLC

(57) ABSTRACT

Methods of loading extracellular vesicles with payload molecules via homogenization are disclosed herein.

11 Claims, 7 Drawing Sheets

(56) References Cited

OTHER PUBLICATIONS

Stewart et al., "In vitro and ex vivo strategies for intracellular delivery," Nature 538(7624):183-192 (2016).
Sutaria et al., "Achieving the promise of therapeutic extracellular vesicles: the devil is in details of therapeutic loading," Pharm Res. 34(5): 1053-1066 (2017).
Visintin et al., "Selection of antibodies for intracellular function using a two-hybrid in vivo system," Proc Natl Acad Sci USA 96(21): 11723-11728 (1999).
Wahlgren et al., "Plasma exosomes can deliver exogenous short interfering RNA to monocytes and lymphocytes," Nucleic Acids Research 40(17): e130 (2012).
Whitehead et al., "Knocking down barriers: advances in siRNA delivery," Nature Reviews Drug Discovery 8(2): 129-138 (2009).
Zhang et al., "Microvesicle-mediated delivery of transforming growth factor beta-1 siRNA for the suppression of tumor growth in mice," Biomaterials 35(14):4390-400 (2014).
United States Patent and Trademark Office, Non-Final Office Action in U.S. Appl. No. 16/190,058, dated Dec. 9, 2019.
United States Patent and Trademark Office, Final Office Action in U.S. Appl. No. 16/190,058, dated May 7, 2020.
United States Patent and Trademark Office, Notice of Abandonment in U.S. Appl. No. 16/190,058, dated Nov. 25, 2020.
United States Patent and Trademark Office, Non-Final Office Action in U.S. Appl. No. 17/014,961, dated Dec. 21, 2021.
United States Patent and Trademark Office, Final Office Action in U.S. Appl. No. 17/014,961, dated Jun. 8, 2022.
United States Patent and Trademark Office, Notice of Abandonment in U.S. Appl. No. 17/014,961, dated Jan. 4, 2023.

\* cited by examiner

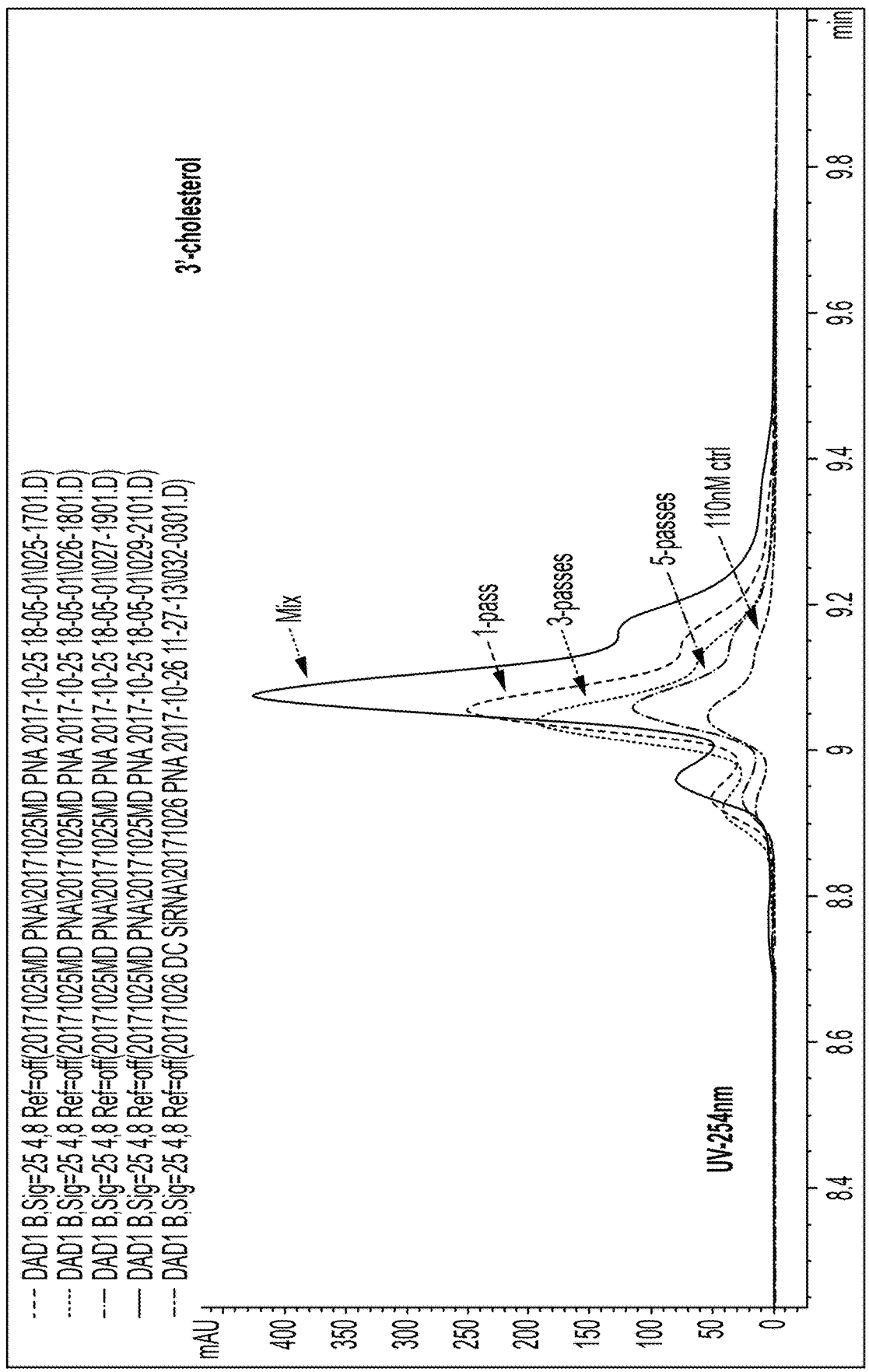

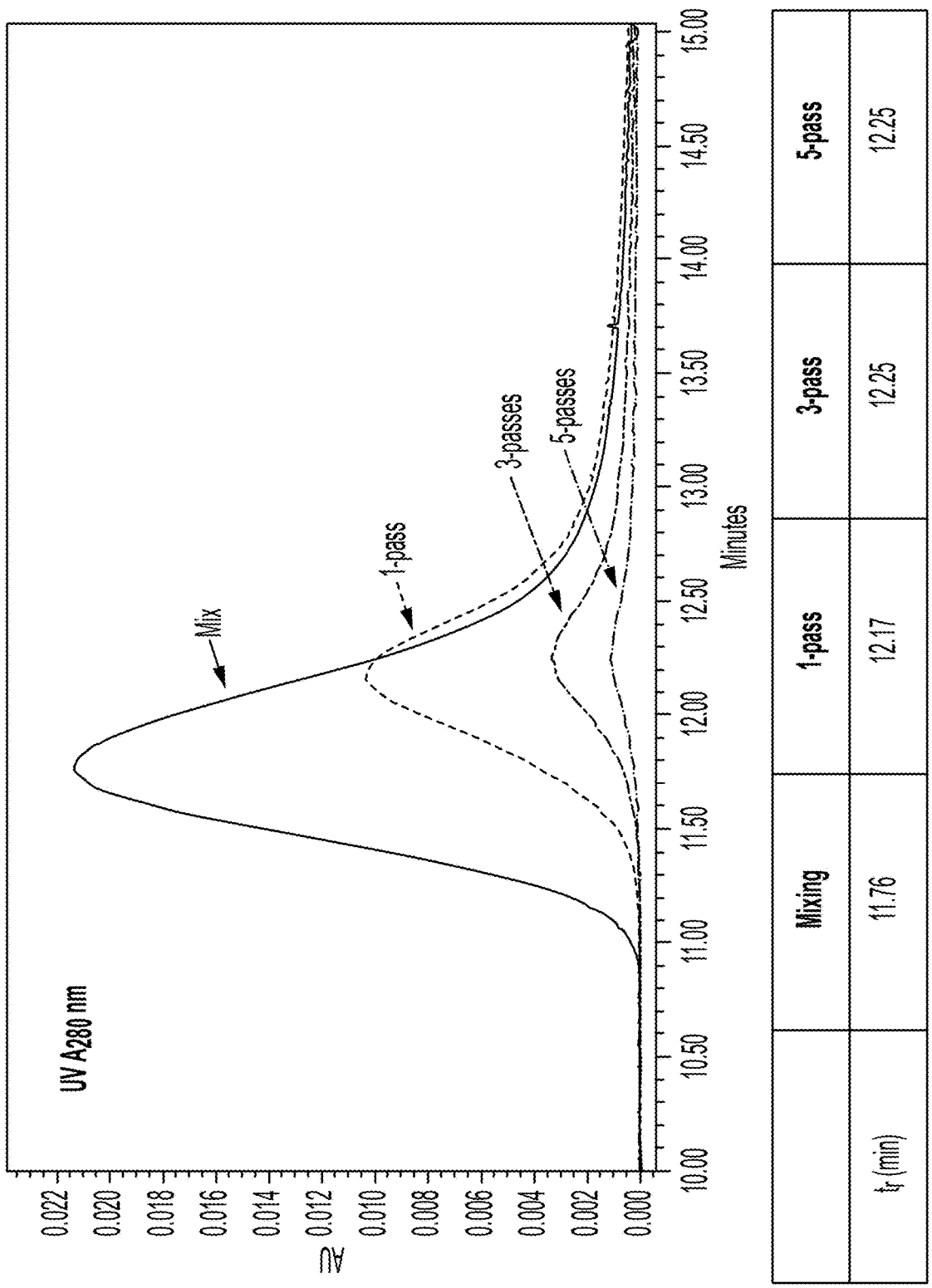

LOADING OF EXTRACELLULAR VESICLES THROUGH IMPARTING OF MECHANICAL SHEAR

CROSS REFERENCE TO RELATED APPLICATIONS

This application claims the benefit of U.S. Provisional Patent Application No. 62/588,143, filed Nov. 17, 2017, the disclosure of which is incorporated by reference in its entirety.

BACKGROUND

There is a need in the field for improved methods and compositions for delivering therapeutic agents to cells. The therapeutic properties of extracellular vesicles can be enhanced by the complexation of a molecule or molecules in a process referred to as loading. Loading represents the encapsulation, partial engulfment, and/or external association of a cargo molecule with the vesicle or vesicles. Methods that facilitate the loading of molecules into or onto vesicles can improve efficiency and enable the loading of diverse classes of molecules. Homogenization, the application of shear and cavitation, can be applied simultaneously to both vesicles and the desired payload to promote loading of the payload into and/or on to the vesicle.

Homogenization, including microfluidization (a branded from of homogenization) has been previously employed for nanoencapsulation and loading of liposomes but has not been used for the loading of vesicles. Provided herein are methods for loading exosomes with therapeutic agents, and the exosomes created by those methods.

SUMMARY OF THE INVENTION

Disclosed herein are methods for producing an isolated extracellular vesicle for delivery of a payload molecule comprising modifying an extracellular vesicle with a payload molecule via homogenization, isolating the modified extracellular vesicle containing the payload molecule, and optionally formulating the isolated modified extracellular vesicle into a pharmaceutical composition. In one embodiment, the vesicle is an exosome, a nanovesicle, an apoptotic body, a microvesicle, a lysosome, an endosome, an enveloped virus, a viral vector, a liposome, a lipid nanoparticle, a micelle, a multilamellar structure, a revesiculated vesicle, or an extruded cell. In another embodiment the payload molecule is a therapeutic molecule. In another embodiment, the vesicle is modified with a plurality of payload molecules.

In some embodiments, the homogenization is microfluidization. In some embodiments, the microfluidization is a single pass. In other embodiments, the microfluidization is multiple passes. In some embodiments, the pressure of the microfluidization is performed between 10,000 to 30,000 pounds per square inch (psi). In one embodiment, the microfluidization is 10,000 psi. In one embodiment, the microfluidization is 20,000 psi. In one embodiment, the microfluidization is 30,000 psi. In some embodiments, the pressure is the same in multiple passes. In other embodiments, the pressure is different in multiple passes.

In some embodiments, the vesicle is in buffered solution. In one embodiment, the solution is between a pH 3 and 13. In another embodiment, the pH of the solution is between 7 and 8. In a further embodiment, the pH of the solution is 7.4. In some embodiments, the buffered solution comprises phosphate buffered saline and 0.5-5% sucrose.

In some embodiments, the volume of the microfluidization is less than a liter. In other embodiments, the volume of the microfluidization is more than a liter. In another embodiment, the volume of the microfluidization is at least 1 ml.

In some embodiments, the microfluidization is performed at 15° C. to 80° C. In another embodiment, the microfluidization is performed at room temperature. In some embodiments, the microfluidization is performed at 70-80° C.

In one embodiment the payload is siRNA, miRNA, antisense RNA, DNA, a plasmid, mRNA, tRNA, a protein, a carbohydrate, a lipid, a small molecule drug, a toxin, an antibody, a recombinant protein, a viral vector, or a vaccine. In another embodiment, the payload is siRNA. In certain embodiments, the payload is a modified nucleic acid. In some embodiments, said modified nucleic acid is an siRNA or miRNA that is modified to additionally comprise one or more cholesterol molecules. In some embodiments, said cholesterol is chemically conjugated to the 5' end of the sense, or passenger strand of the siRNA or miRNA. In some embodiments, said cholesterol is chemically conjugated to the 3' end of the sense, or passenger strand of the siRNA or miRNA. In some embodiments, said cholesterol is chemically conjugated to the 5' end of the antisense, or guide strand of the siRNA or miRNA. In some embodiments, said cholesterol is chemically conjugated to the 3' end of the antisense, or guide strand of the siRNA or miRNA.

In some embodiments, a solution comprising the vesicle and the payload are first mixed and the mixture is homogenized. In some embodiments, a solution comprising the vesicle is homogenized first and the payload is added to the homogenized vesicle solution.

In some embodiments, the vesicle is modified with a plurality of payload molecules.

In one embodiment, the payload molecules are predominantly on the surface of the modified vesicle. In another embodiment, the payload molecules are predominantly inside the modified vesicle.

In some embodiments, the vesicle in solution is both homogenized and treated with another technology for loading the payload molecules. In one embodiment, the additional treatment is a chemical treatment. In one embodiment, vesicle is post-treated after homogenization. In another embodiment, the vesicle is pre-treated before homogenization.

The vesicles may be homogenized in a batch, a semi-batch, or a continuous process.

BRIEF DESCRIPTION OF THE DRAWINGS

FIGS. 4A-B show the anion exchange chromatogram profile of unmodified siRNA (4A) and cholesterol-tagged siRNA (4B) after repeated rounds of microfluidic homogenization.

FIGS. 5A-B show the results from measuring the diameter of purified exosomes after repeated rounds of microfluidic homogenization as determined by size exclusion chromatography (5A) and nanoparticle tracking assay (5B).

DETAILED DESCRIPTION

Definitions

Figure 1:
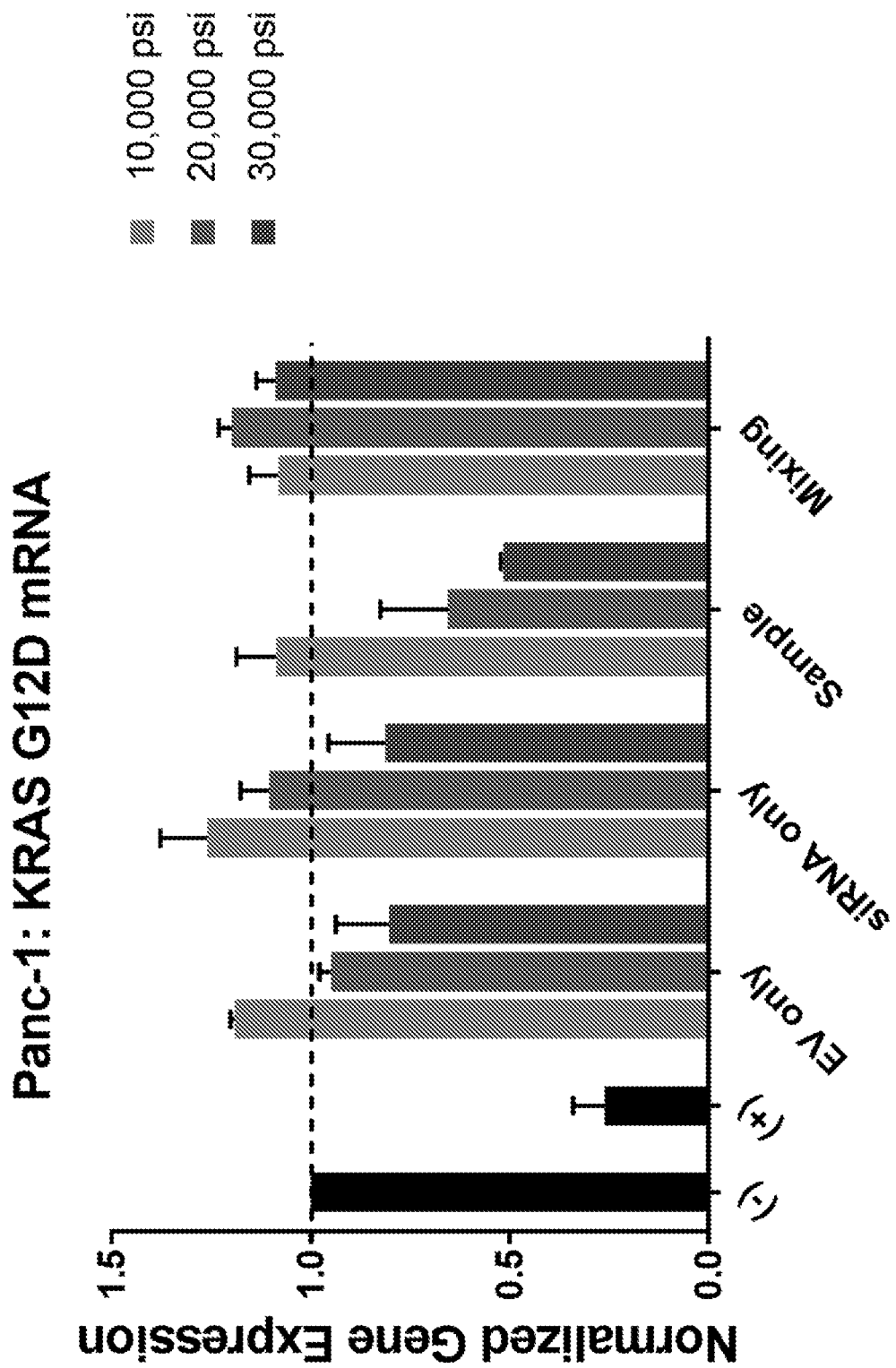
FIG. 1 shows the qPCR results from kras gene knockdown cell based assay in Panc-1 cells as a function of shear pressure. The left bar shows samples homogenized at 10,000 psi, the middle bar shows the samples homogenized at 20,000 psi, and the right bar shows the samples homogenized at 30,000 psi.

Terms used in the claims and specification are defined as set forth below unless otherwise specified.

As used herein, the term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and may comprise various macromolecular cargo either within the internal space, displayed on the external surface of the extracellular vesicle, and/or spanning the membrane. Said cargo may comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles may be derived from a living or dead organism, explanted tissues or organs, and/or cultured cells.

As used herein, the term "nanovesicle" refers to a cell-derived small (between 20-250 nm in diameter, more preferably 30-150 nm in diameter) vesicle comprising a membrane that encloses an internal space, and which is generated from said cell by direct or indirect manipulation such that said nanovesicle would not be produced by said producer cell without said manipulation. Appropriate manipulations of said producer cell include but are not limited to serial extrusion, treatment with alkaline solutions, sonication, or combinations thereof. The production of nanovesicles may, in some instances, result in the destruction of said producer cell. Preferably, populations of nanovesicles are substantially free of vesicles that are derived from producer cells by way of direct budding from the plasma membrane or fusion of the late endosome with the plasma membrane. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to said manipulation, may be isolated from the producer cell based on its size, density, biochemical parameters, or a combination thereof.

As used herein, the term "exosome" refers to a cell-derived small (between 20-300 nm in diameter, more preferably 40-200 nm in diameter) vesicle comprising a membrane that encloses an internal space, and which is generated from said cell by direct plasma membrane budding or by fusion of the late endosome with the plasma membrane. Generally, production of exosomes does not result in the destruction of the producer cell. The exosome comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof.

As used herein, the terms "parent cell" or "producer cell" include any cell from which an extracellular vesicle may be isolated. The terms also encompasses a cell that shares a protein, lipid, sugar, or nucleic acid component of the extracellular vesicle. For example, a "parent cell" or "producer cell" may include a cell which serves as a source for the extracellular vesicle membrane.

As used herein, the terms "purify," "purified," and "purifying" or "isolate," "isolated," or "isolating" or "enrich," "enriched" or "enriching" are used interchangeably and refer to the state of a population (e.g., a plurality of known or unknown amount and/or concentration) of desired extracellular vesicles, that have undergone one or more processes of purification, e.g., a selection or an enrichment of the desired extracellular vesicles composition, or alternatively a removal or reduction of residual biological products as described herein. In some embodiments, a purified extracellular vesicles composition has no detectable undesired activity or, alternatively, the level or amount of the undesired activity is at or below an acceptable level or amount. In other embodiments, a purified extracellular vesicle composition has an amount and/or concentration of desired extracellular vesicles at or above an acceptable amount and/or concentration. In other embodiments, the purified extracellular vesicle composition is enriched as compared to the starting material (e.g., biological material collected from tissue, bodily fluid, or cell preparations) from which the composition is obtained. This enrichment may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material.

A "payload" as used herein is a therapeutic agent that acts on a target (e.g. a target cell) that is contacted with the extracellular vesicles. Payloads that may be introduced into a extracellular vesicles and/or a producer cell include therapeutic agents such as, nucleotides (e.g. nucleotides comprising a detectable moiety or a toxin or that disrupt transcription), nucleic acids (e.g. DNA or mRNA molecules that encode a polypepetide such as an enzyme, or RNA molecules that have regulatory function such as miRNA, dsDNA, lncRNA, siRNA), amino acids (e.g. amino acids comprising a detectable moiety or a toxin or that disrupt translation), polypeptides (e.g. enzymes), lipids, carbohydrates, and small molecules (e.g. small molecule drugs and toxins). The payload may comprise nucleotides, e.g. nucleotides that are labeled with a detectable or cytotoxic moiety (e.g. a radiolabel).

"Transgene" or "exogenous nucleic acid" refers to a foreign or native nucleotide sequence that is introduced into an extracellular vesicle. Transgene and exogenous nucleic acid are used interchangeably herein and encompass recombinant nucleic acids.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

The term "pharmaceutically-acceptable" and grammatical variations thereof, refers to compositions, carriers, diluents and reagents capable of administration to or upon a subject without the production of undesirable physiological effects to a degree that would prohibit administration of the composition.

As used herein, the term "pharmaceutical composition" refers to one or more of the compounds described herein, such as, e.g., an extracellular vesicles mixed or intermingled with, or suspended in one or more other chemical components, such as pharmaceutically acceptable carriers and excipients. One purpose of a pharmaceutical composition is to facilitate administration of preparations of extracellular vesicles to a subject.

The term "about" indicates and encompasses an indicated value and a range above and below that value. In certain embodiments, the term "about" indicates the designated value ±10%, ±5%, or ±1%. In certain embodiments, where applicable, the term "about" indicates the designated value(s)±one standard deviation of that value(s).

It must be noted that, as used in the specification and the appended claims, the singular forms "a," "an" and "the" include plural referents unless the context clearly dictates otherwise.

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Methods of the Invention

Methods of Loading Extracellular Vesicles

Described herein are methods for producing modified extracellular vesicles via mechanical shear such as homogenization and pharmaceutical preparations thereof. Extracellular vesicles can include, but are not limited to, an exosome, a nanovesicle, an apoptotic body, a microvesicle, a lysosome, an endosome, an enveloped virus, a viral vector, a liposome, a lipid nanoparticle, a micelle, a multilamellar structure, a revesiculated vesicle, or an extruded cell.

Homogenization, the application of shear and cavitation, can stress the vesicular structure resulting in many effects, including distortion to the phospholipid membrane and associated cytoskeleton leading to the creation of transient pores; and increase permeability, exposure of binding sites, and/or invagination of the surface. Homogenization may also lead to disaggregation of lipid rafts leading to increased permeability and membrane fluidity; formation of multilamellar bodies, both through invagination and disaggregation; conformational shifts in peripheral and transmembrane proteins that expose binding sites, alter surface properties, and enable the transmembrane passage of molecules; heat the vesicular membrane and alter permeability, fluidity, and diffusion; and/or denature proteins that permanently affect the structure of the membrane. Homogenization may also alter the surface properties of the molecule to be loaded or cause shifts in the chemical equilibria and local concentrations of molecules, leading to steeper concentration gradients. These effects may facilitate the loading of molecules into or onto vesicles, and improve the efficiency of loading diverse classes of molecules.

Generally, any homogenization method that induces controlled injury may be used to load an agent, e.g. a payload molecule, receiver or surface marker into or onto an extracellular vesicle. The homogenization of the membrane of the producer cell or extracellular vesicles can be caused by, for example, pressure induced by mechanical strain or shear forces, subjecting the cell to deformation, constriction, rapid stretching, rapid compression, or pulse of high shear rate. The controlled injury leads to uptake of material, e.g., a payload, receiver or surface marker into the interior of the extracellular vesicles or the cytoplasm of the producer cell from the surrounding cell medium.

Many different homogenization instruments are available, including microfluidizers, French Press, high pressure homogenizers, bead mills, rotary blenders and rotor/stator devices. In some embodiments described herein, vesicles may be homogenized using a microfluidizer. Microfluidizers may be purchased from commercial sources, such as the LV1 Microfluidizer made by Idex Corporation (Newton, MA) or the M110P homogenization module made by Microfluidics Corp (Westwood, MA)

A microfluidizer consists of a fixed-geometry interaction chamber in which flow is driven by a pump. The incoming flow is split into two or more streams and the recombined at high velocity to create steep velocity and pressure gradients, shear, cavitation, and heating. The intensity of homogenization can be altered by changing the geometry of the interaction chamber, altering the temperature, changing the pressure, or processing the same material through the instrument multiple times. There is also a complex interaction with the concentration of the incoming material, buffer composition, and the physiochemical properties of the solution, emulsion, or suspension.

Several parameters may affect loading of the payload molecule, including pressure, temperature, number of homogenization passes, and buffer conditions. The pressure of the microfluidization can be from about 5,000 to 50,000 psi. The pressure of the microfluidization can be at least about 5,000 psi, 10,000 psi, 15,000 psi, 20,000 psi, 25,000 psi, 20,000 psi, 25,000 psi, 40,000 psi, 45,000 psi, or 50,000 psi. The pressure of the microfluidization can be between about 5,000 to 50,000 psi, 5,000 to 10,000 psi, 7,500 to 12,000 psi, 10,000 to 15,000 psi, 15,000 to 20,000 psi, 15,000-22,000, psi, 18,000-25,000 psi, 18,000-22,000 psi, 20,000 to 25,000 psi, 25,000 to 30,000 psi, 27,500 to 30,000 psi, 27,500 to 32,000 psi, 30,000 to 32,000 psi, 30,000 to 35,000 psi, 35,000 to 40,000 psi, 40,000 to 45,000 psi, or 45,000 to 50,000 psi. In some embodiments disclosed herein, the pressure of the homogenization or microfluidization is about 10,000 psi, 20,000 psi, or 30,000 psi. In one embodiment, the pressure is between 10,000 and 30,000 psi.

The homogenization or microfluidization may be a single pass or run, or comprise multiple passes or runs. In one embodiment, the pressure of one or more of the multiple passes or runs may be that same for each pass. For example, the pressure of the first pass can be about 10,000 psi and the pressure of the second pass can be about 10,000 psi; the pressure of the first pass can be about 20,000 psi and the pressure of the second pass can be about 20,000 psi; or the pressure of the first pass can be about 30,000 psi and the pressure of the second pass can be about 30,000 psi; or any of the microfluidization pressures disclosed herein. Multiple passes can be two or more passes, such as three passes, four passes, five passes, six passes, seven passes, eight passes, and so on. In another embodiment, the pressure of one or more of the multiple passes or runs may be different. For example, the pressure of the first pass can be about 10,000 psi and the pressure of the second pass can be about 20,000 psi; the pressure of the first pass can be about 20,000 psi and the pressure of the second pass can be about 30,000 psi; the pressure of the first pass can be about 30,000 psi and the pressure of the second pass can be about 20,000 psi; or the pressure of the first pass can be about 10,000 psi and the pressure of the second pass can be about 30,000 psi, or any combination of the microfluidization pressures disclosed herein. Multiple passes can be two or more passes, such as three passes, four passes, five passes, six passes, seven passes, eight passes, and so on.

The buffer conditions of the solution of extracellular vesicles may also be altered to optimize homogenization and payload molecule loading. In one embodiment, the buffer may be a phosphate buffered saline (PBS) with sucrose. PBS is a well-known buffer to those skilled in the art. In one embodiment, the PBS buffer also comprises 0.5-5% sucrose. The buffer can comprise about 0.5-5%, 0.5-1%, 1-2%, 2-3%, 3-4%, 4-5%, 1%, 1.5%, 2%, 2.5%, 3%, 3.5%, 4%, 4.5% or 5% sucrose. Additional buffer modifications may also be used, such as shear protectants, viscosity modifiers, and/or solutes that affect vesicle structural properties. Excipients may also be added to improve the efficiency of the homogenization or microfluidization such as membrane softening materials and molecular crowding agents. Other modifications to the buffer may include specific pH ranges and/or concentrations of salts, organic solvents, small molecules, detergents, zwitterions, amino acids, polymers, and/or any combination of the above including multiple concentrations.

The pH of the buffer may also be altered. The pH can be between 3-13, 3-5, 5-10, 7-8, 8-10, 10-13. The pH can be about 3, 3.5, 4, 4.5, 5, 5.5, 6, 6.5, 6.8, 7, 7.2, 7.4, 7.5, 7.6, 7.8, 8, 8.2, 8.4, 8.5, 9, 9.5, 10, 10.5, 11, 11.5, 12, 12.5, or 13. In one embodiment, the pH is between 3 and 13. In one embodiment, the pH is between 7 and 8. In a further embodiment, the pH is 7.4.

The temperature of the homogenization or microfluidization may be changed for optimization of loading the payload molecules. The temperature can be between about 15-90° C., 15-20° C., 20-25° C., 25-30° C., 30-35° C., 35-40° C., 45-50° C., 50-55° C., 55-60° C., 60-65° C., 65-70° C., 70-75° C., 75-80° C., 80-85° C., or 85-90° C. The temperature can be about 15° C., 20° C., 25° C., 27° C., 30° C., 32° C., 35° C., 40° C., 45° C., 50° C., 55° C., 60° C., 65° C., 70° C., 75° C., 80° C., 85° C., or 90° C. In one embodiment, the temperature may be room temperature. In another embodiment, the temperature is 15° C. to 80° C. In another embodiment, the temperature is 70-80° C.

The volume of the solution comprising extracellular vesicles to be homogenized or microfluidized may also be altered. The volume can be from about 1 ml to about 5000 ml, or more. The volume can be at least about 1-10 ml, 10-50 ml, 50-100 ml, 100-150 ml, 150-200 ml, 200-250 ml, 250-300 ml, 300-350 ml, 350-400 ml, 400-450 ml, 450-500 ml, 500-550 ml, 550-600 ml, 600-650 ml, 650-700 ml, 750-800 ml, 800-850 ml, 850-900 ml, 950-1000 ml, 1000-1500 ml, 1500-2000 ml, 2000-2500 ml, 2500-3000 ml, 3000-3500 ml, 3500-4000 ml, 4000-4500 ml, 45000-5000 ml, or more. The volume can be at least about 1 ml, 10 ml, 20 ml, 30 ml, 40 ml, 50 ml, 60 ml, 70 ml, 80 ml, 90 ml, 100 ml, 150 ml, 200 ml, 250 ml, 300 ml, 350 ml, 400 ml, 450 ml, 500 ml, 550 ml, 600 ml, 650 ml, 700 ml, 750 ml, 800 ml, 850 ml, 900 ml, 950 ml, 1000 ml, 1500 ml, 2000 ml, 2500 ml, 3000 ml, 3500 ml, 4000 ml, 4500, ml or 5000 ml. In one embodiment, the volume is less than a liter. In another embodiment, the volume is more than a liter. In another embodiment, the volume of the solution may be at least 1 ml.

The extracellular vesicles may also be treated with additional technologies before or after homogenization. In one embodiment, the vesicles are pre-treated before homogenization. In one embodiment, the vesicles are post-treated after homogenization. The treatment may include a chemical treatment, such as acidic or basic buffers, or other chemical treatments not described herein.

The extracellular vesicle may be modified with a single payload molecule or with a plurality of payload molecules. A detailed description of such payload molecules is disclosed below. In one embodiment, the extracellular vesicles may be modified with a plurality of payload molecules. The payload molecules may be the same type or class of molecule, or a different type or class of molecule. Multiple types of payload molecules may be combined to produce vesicles modified with multivalent payload molecule cargoes. For example, the vesicle can have two types, three types, four types, five types, six types, and so on. In another embodiment, the payload molecules may be predominantly on the surface of the modified vesicle. In another embodiment, the payload molecules may be predominantly inside the modified vesicle. The extracellular vesicles to be modified may be homogenized first and the payload molecules added to the homogenized vesicle solution. In a further embodiment, the extracellular vesicles and the payload molecules are mixed together and the mixture is homogenized.

The homogenization may be applied in a batch mode, a semi-batch mode, or a continuous process. Either batch or continuous process may rely on feedback to control the homogenization or microfluidization parameters and/or terminate the process.

Extracellular Vesicles

Extracellular vesicles can be extracted from the supernatant of parent cells and demonstrate membrane and internal protein, lipid, and nucleic acid compositions that enable their efficient delivery to and interaction with recipient cells. Extracellular vesicles can be derived from parent cells that may include, but are not limited to, reticulocytes, erythrocytes, megakaryocytes, platelets, neutrophils, tumor cells, connective tissue cells, neural cells and stem cells. Suitable sources of extracellular vesicles include but are not limited to, cells isolated from subjects from patient-derived hematopoietic or erythroid progenitor cells, immortalized cell lines, or cells derived from induced pluripotent stem cells, optionally cultured and differentiated. Cell culture protocols can vary according to compositions of nutrients, growth factors, starting cell lines, culture period, and morphological traits by which the resulting cells are characterized. In some embodiments, the samples comprising extracellular vesicles are derived from a plurality of donor cell types (e.g., 2, 3, 4, 5, 6, 7, 8, 9, 10, 50, 100, 500, 1000, 5000, or 10000 donor cell types) and are combined or pooled. Pooling may occur by mixing cell populations prior to extracellular vesicles extraction or by mixing isolated extracellular vesicles compositions from subsets of donor cell types. Parent cells may be irradiated or otherwise treated to affect the production rate and/or composition pattern of secreted extracellular vesicles prior to isolation.

In some embodiments, the extracellular vesicle comprises a membrane that forms a particle that has a diameter of between about 10-100 nm, 50-150 nm, 30-100 nm, 40-100 nm, 20-150 nm, 20-200 nm, 80-125 nm, 40-250 nm, 20-500 nm, or between about 10-1000 nm. The vesicle particle can have diameter of about 10, 150, 100, 120, 125, 130, 135, 140, 145, 150, 155, 160, 175, 200, 225, 250, 275, 300, 325, 250, 275, 400, 425, 450, 475, 500, 525, 550, 575, 600, 625, 650, 675, 700, 725, 750, 775, 800, 825, 850, 875, 900, 925, 950, 975, or 1000 nm. In some embodiments, the membrane comprises lipids and fatty acids. In some embodiments, the membrane comprises one or more of phospholipids, glycolipids, fatty acids, sphingolipids, phosphoglycerides, sterols, cholesterols, and phosphatidylserine. In addition, the membrane may comprise one or more polypeptides and one or more polysaccharides, such as glycans.

In some embodiments, the extracellular vesicle is generated by a producer cell (or parental cell), such as, e.g., a mammalian cell. In some embodiments, the membrane of the extracellular vesicle comprises one or more molecules derived from the producer cell. The extracellular vesicle may be generated in a cell culture system and isolated, e.g. by separating the extracellular vesicle from the producer cell. Separation may be achieved by sedimentation. For example, the extracellular vesicle can have a specific density between 0.5-2.0, 0.5-0.75, 0.5-1, 0.75-1.5, 0.75-2, 1-2, 1.5-2, and 0.9-1.1 kg/m3. The extracellular vesicle can have a specific density about 0.5, 0.75, 1, 1.25, 1.5, 1.75, or 2 kg/m3.

In some embodiments, the extracellular vesicle delivers the payload molecule to a target. The payload molecule is a therapeutic agent that acts on a target (e.g. a target cell) that is contacted with the extracellular vesicle. Contacting may occur, e.g. in vitro or in a subject. Payloads that may be introduced into an extracellular vesicle and/or a producer cell include therapeutic agents such as, nucleotides (e.g. nucleotides comprising a detectable moiety or a toxin or that disrupt transcription), nucleic acids (e.g. DNA or mRNA molecules that encode a polypepetide such as an enzyme, or RNA molecules that have regulatory function such as miRNA, dsDNA, lncRNA, siRNA), amino acids (e.g. amino acids comprising a detectable moiety or a toxin or that disrupt translation), polypeptides (e.g. enzymes), lipids, carbohydrates, and small molecules (e.g. small molecule drugs and toxins). The payload may comprise nucleotides, e.g. nucleotides that are labeled with a detectable or cytotoxic moiety (e.g. a radiolabel).

In some embodiments, the extracellular vesicle comprises nucleotides and/or polynucleotides (e.g. nucleic acids). For example, the extracellular vesicle may comprise RNA, DNA, mRNA, miRNA, dsDNA, lncRNA, siRNA, or singular nucleotides. In some embodiments, the nucleotides and polynucleotides are synthetic. For example, an exogenous nucleic acid may be introduced into the extracellular vesicle and/or the producer cell. In some embodiments, the nucleic acid is DNA that can be transcribed into an RNA (e.g. an siRNA or mRNA) and in the case of an mRNA may be translated into a desired polypeptide. In some embodiments, the nucleic acid is an RNA (e.g. an siRNA or mRNA) and in the case of an mRNA may be translated into a desired polypeptide.

In some embodiments, the extracellular vesicle comprises a nucleic acid, such as a RNA or DNA. The nucleic acid is delivered to a target cell as a payload. The target cell may transcribe a DNA payload into an RNA such as a siRNA. In case an mRNA is transcribed by the target cell form the DNA payload, the cell may translate the mRNA into a polypeptide (e.g. therapeutic polypeptide). The target cell may also translate a delivered mRNA payload into a polypeptide.

In some embodiments, the producer cell comprises a nucleic acid that may be transcribed (e.g. a DNA may be transcribed into a siRNA or mRNA) and in case a mRNA is made the mRNA may be translated by the producer cell into a polypeptide. The producer cell may also be modified with a non-translatable RNA (e.g. siRNA or miRNA). In case a mRNA is transferred the producer cell may translate the mRNA into a polypeptide. Extracellular vesicles derived from the producer cell may then carry the non-translatable RNA, the transcribed RNA or the translated polypeptide as a payload. In certain embodiments, the nucleic acid payload is a modified nucleic acid. In some embodiments, said modified nucleic acid is an siRNA or miRNA that is modified to additionally comprise one or more cholesterol molecules. The cholesterol modifications on the nucleic acid payloads may increase the association between the nucleic acid and the inner and/or outer membrane of the extracellular vesicles, therefore increasing the maximal loading capacity of the extracellular vesicles. In some embodiments, said cholesterol is chemically conjugated to the 5' end of the sense, or passenger strand of the siRNA or miRNA. In some embodiments, said cholesterol is chemically conjugated to the 3' end of the sense, or passenger strand of the siRNA or miRNA. In some embodiments, said cholesterol is chemically conjugated to the 5' end of the antisense, or guide strand of the siRNA or miRNA. In some embodiments, said cholesterol is chemically conjugated to the 3' end of the antisense, or guide strand of the siRNA or miRNA.

The extracellular vesicles may interact with the target cell via membrane fusion and deliver payloads (e.g., therapeutic agents) in an extracellular vesicle composition to the surface or cytoplasm of a target cell. In some embodiments, membrane fusion occurs between the extracellular vesicles and the plasma membrane of a target cell. In other embodiments, membrane fusion occurs between the extracellular vesicles and an endosomal membrane of a target cell.

Methods of Isolating Extracellular Vesicles

The extracellular vesicles may be isolated from the producer cells. It is contemplated that all known manners of isolation of extracellular vesicles are deemed suitable for use herein. For example, physical properties of extracellular vesicles may be employed to separate them from a medium or other source material, including separation on the basis of electrical charge (e.g., electrophoretic separation), size (e.g., filtration, molecular sieving, etc), density (e.g., regular or gradient centrifugation), Svedberg constant (e.g., sedimentation with or without external force, etc). Alternatively, or additionally, isolation may be based on one or more biological properties, and include methods that may employ surface markers (e.g., for precipitation, reversible binding to solid phase, FACS separation, specific ligand binding, non-specific ligand binding, etc.). In yet further contemplated methods, the extracellular vesicles may also be fused using chemical and/or physical methods, including PEG-induced fusion and/or ultrasonic fusion.

Isolation (and enrichment) can be done in a general and non-selective manner (typically including serial centrifugation). Alternatively, isolation and enrichment can be done in a more specific and selective manner (e.g., using producer cell-specific surface markers). For example, specific surface markers may be used in immunoprecipitation, FACS sorting, affinity purification, bead-bound ligands for magnetic separation etc.

In certain preferred embodiments, isolation can be done by affinity purification. For example, the extracellular vesicle can be purified by binding a population comprising extracellular vesicles to a resin, said resin comprising a plurality of ligands that have specific affinity for one or more target proteins on the surface of the extracellular vesicle. The one or more target protein may be a tetraspanin (e.g., CD63, CD81 and/or CD9), an EWI protein/immunoglobulin superfamily member (e.g., PTGFRN, IGSF8 and/or IGSF3), an integrin (e.g., ITGB1 and/or ITGA4), an ATP transporter protein (e.g., ATP1A1, ATP1A2, ATP1A3, ATP1A4, ATP1B3, ATP2B1, ATP2B2, ATP2B3 and/or ATP2B4), SLC3A2, BSG, or CD98hc. The target protein may additionally be the immunomodulating component that is displayed on the surface of the exosomes.

In some embodiments, size exclusion chromatography can be utilized to isolate the extracellular vesicles. Size exclusion chromatography techniques are known in the art. Exemplary, non-limiting techniques are provided herein. In some embodiments, a void volume fraction is isolated and comprises the extracellular vesicles of interest. Further, in some embodiments, the extracellular vesicles can be further isolated after chromatographic separation by centrifugation techniques (of one or more chromatography fractions), as is generally known in the art. In some embodiments, for example, density gradient centrifugation can be utilized to further isolate the extracellular vesicles. Still further, in some embodiments, it can be desirable to further separate the producer cell-derived extracellular vesicles from extracellular vesicles of other origin. For example, the producer cell-derived extracellular vesicles can be separated from non-producer cell-derived extracellular vesicles by immunosorbent capture using an antigen antibody specific for the producer cell.

In some embodiments, the isolation of extracellular vesicles may involve combinations of methods that include, but are not limited to, differential centrifugation, size-based membrane filtration, concentration and/or rate zonal centrifugation.

Particle size may be quantified after the extracellular vesicles are isolated using any appropriate technique, including dynamic light scattering or nanoparticle tracking analysis. The diameter of the extracellular vesicles in a population can also be described using particle size distribution (D values). D values reflect the mass of the extracellular vesicles in a population as a percentage when the particles are arranged on an ascending mass basis. For instance, the D10 value is the diameter at which 10% of the extracellular vesicles population mass is comprised of extracellular vesicles less than the indicated diameter value. In such a case, the population of extracellular vesicles is comprised mainly of vesicles larger than the indicated diameter value. The D50 value is the diameter at which 50% of the extracellular vesicles population mass is comprised of vesicles less than the indicated diameter value and 50% of the extracellular vesicles population mass is comprised of vesicles larger than the indicated value. In such a case, the population of extracellular vesicles is comprised equally of vesicles larger than the indicated diameter value and smaller than the indicated diameter. The D90 value is the diameter at which 90% of the extracellular vesicles population mass is comprised of extracellular vesicles less than the indicated diameter value. In this case, the population of extracellular vesicles is comprised mainly of vesicles smaller than the indicated diameter value.

Payload Molecules

Extracellular vesicles may comprise payloads such as peptides, proteins, DNA, RNA, siRNA, and other macromolecules and small therapeutic molecules. In some embodiments, the payload is transferred to a producer cell by applying controlled injury to the cell for a predetermined amount of time in order to cause perturbations in the cell membrane such that the payload can be delivered to the inside of the cell (e.g., cytoplasm). In some embodiments the payload is transferred to a extracellular vesicles isolated from a producer cell by applying controlled injury to the extracellular vesicles for a predetermined amount of time in order to cause perturbations in the complex membrane such that the payload can be delivered to the inside of the extracellular vesicles. In some embodiments the payload of the extracellular vesicles may be loaded within the membrane or interior portion of the extracellular vesicles.

The payload may be a therapeutic agent selected from a variety of known small molecule pharmaceuticals. Alternatively, the payload may be a therapeutic agent selected from a variety of macromolecules, such as, e.g., an inactivating peptide nucleic acid (PNA), an RNA or DNA oligonucleotide aptamer, an interfering RNA (iRNA), a peptide, or a protein.

In some embodiments, the payload that may be delivered to a target by a extracellular vesicles includes, but is not limited to, RNA, DNA, siRNA, mRNA, lncRNA, iRNA, polypeptides, enzymes, cyotkines, antibodies, antibody fragments, small molecules, chemotherapeutics, metals, viral particles, imaging agents, and plasmids.

In some embodiments the payload of the extracellular vesicles is a nucleic acid molecule, e.g. mRNA or DNA, and the extracellular vesicles targets the payload to the cytoplasm of the recipient or target cell, such that the nucleic acid molecule can be translated (if mRNA) or transcribed and translated (if DNA) and thus produce the polypeptide encoded by the payload nucleic acid molecule within the target cell. In one embodiment the polypeptide encoded by the payload nucleic acid molecule is secreted by the target cell, thus modulating the systemic concentration or amount of the polypeptide encoded by the payload nucleic acid molecule in the subject. In one embodiment the polypeptide encoded by the payload nucleic acid molecule is not secreted by the target cell, thus modulating the intracellular concentration or amount of the polypeptide encoded by the payload nucleic acid molecule in the subject. In one embodiment the polypeptide encoded by the payload nucleic acid molecule is toxic to the target cell or to other cell or tissue in the subject, e.g. toxic to a cancer cell. In one embodiment, the polypeptide encoded by the payload nucleic acid molecule is not toxic to the target cell or other cell or tissue in the subject, e.g. is therapeutically beneficial or corrects a disease phenotype.

In some embodiments the payload of the extracellular vesicles may be a membrane protein delivered to the plasma membrane or endosomal membrane of the recipient cell.

Extracellular vesicles may comprise two or more payloads, including mixtures, fusions, combinations and conjugates, of atoms, molecules, etc. as disclosed herein, for example including but not limited to, a nucleic acid combined with a polypeptide; two or more polypeptides conjugated to each other; a protein conjugated to a biologically active molecule (which may be a small molecule such as a prodrug); and the like.

Suitable payloads include, without limitation, pharmacologically active drugs and genetically active molecules, including antineoplastic agents, anti-inflammatory agents, hormones or hormone antagonists, ion channel modifiers, and neuroactive agents. Examples of suitable payloads of therapeutic agents include those described in, "The Pharmacological Basis of Therapeutics," Goodman and Gilman, McGraw-Hill, New York, N.Y., (1996), Ninth edition, under the sections: Drugs Acting at Synaptic and Neuroeffector Junctional Sites; Drugs Acting on the Central Nervous System; Autacoids: Drug Therapy of Inflammation; Water, Salts and Ions; Drugs Affecting Renal Function and Electrolyte Metabolism; Cardiovascular Drugs; Drugs Affecting Gastrointestinal Function; Drugs Affecting Uterine Motility; Chemotherapy of Parasitic Infections; Chemotherapy of Microbial Diseases; Chemotherapy of Neoplastic Diseases; Drugs Used for Immunosuppression; Drugs Acting on Blood-Forming organs; Hormones and Hormone Antagonists; Vitamins, Dermatology; and Toxicology, all incorporated herein by reference. Suitable payloads further include toxins, and biological and chemical warfare agents, for example see Somani, S. M. (ed.), Chemical Warfare Agents, Academic Press, New York (1992)).

In some embodiments, the payload is a therapeutic agent, such as a small molecule drug or a large molecule biologic. Large molecule biologics include, but are not limited to, a protein, polypeptide, or peptide, including, but not limited to, a structural protein, an enzyme, a cytokine (such as an interferon and/or an interleukin), a polyclonal or monoclonal antibody, or an effective part thereof, such as an Fv fragment, which antibody or part thereof, may be natural, synthetic or humanized, a peptide hormone, a receptor, or a signaling molecule. In certain embodiments, the protein payload is a Cas9 protein, a TALEN, a zinc finger nuclease, or other component of a genome-editing complex.

Large molecule biologics are immunoglobulins, antibodies, Fv fragments, etc., that are capable of binding to antigens in an intracellular environment. These types of molecules are known as "intrabodies" or "intracellular antibodies." An "intracellular antibody" or an "intrabody" includes an antibody that is capable of binding to its target or cognate antigen within the environment of a cell, or in an environment that mimics an environment within the cell. Selection methods for directly identifying such "intrabodies" include the use of an in vivo two-hybrid system for selecting antibodies with the ability to bind to antigens inside mammalian cells. Such methods are described in PCT/GB00/00876, incorporated herein by reference. Techniques for producing intracellular antibodies, such as anti-(3-galactosidase scFvs, have also been described in Martineau et al., J Mol Biol 280:117-127 (1998) and Visintin et al., Proc. Natl. Acad. Sci. USA 96:11723-1728 (1999).

Large molecule biologics include but is not limited to, at least one of a protein, a polypeptide, a peptide, a nucleic acid, a virus, a virus-like particle, an amino acid, an amino acid analogue, a modified amino acid, a modified amino acid analogue, a steroid, a proteoglycan, a lipid and a carbohydrate or a combination thereof (e.g., chromosomal material comprising both protein and DNA components or a pair or set of effectors, wherein one or more convert another to active form, for example catalytically).

A large molecule biologic may include a nucleic acid, including, but not limited to, an oligonucleotide or modified oligonucleotide, an antisense oligonucleotide or modified antisense oligonucleotide, an aptamer, a cDNA, genomic DNA, an artificial or natural chromosome (e.g., a yeast artificial chromosome) or a part thereof, RNA, including an siRNA, a shRNA, mRNA, tRNA, rRNA or a ribozyme, or a peptide nucleic acid (PNA); a virus or virus-like particles; a nucleotide or ribonucleotide or synthetic analogue thereof, which may be modified or unmodified. Said modification may be a lipophilic modification including addition of a cholesterol molecule, myristoylation, PEGylation, and/or palmitoylation.

The large molecule biologic can also be an amino acid or analogue thereof, which may be modified or unmodified or a non-peptide (e.g., steroid) hormone; a proteoglycan; a lipid; or a carbohydrate. If the large molecule biologic is a polypeptide, it can be loaded directly into a producer cell according to the methods described herein. Alternatively, an exogenous nucleic acid encoding a polypeptide, which sequence is operatively linked to transcriptional and translational regulatory elements active in a producer cell at a target site, may be loaded.

Small molecules, including inorganic and organic chemicals, may also be used as payloads of the extracellular vesicles described herein.

In some embodiments, the small molecule is a pharmaceutically active agent. Useful classes of pharmaceutically active agents include, but are not limited to, antibiotics, anti-inflammatory drugs, angiogenic or vasoactive agents, growth factors and chemotherapeutic (antineoplastic) agents (e.g., tumour suppressers).

In some embodiments, the payload molecule comprises an agonist or activator of stimulator of interferon genes (STING). The STING agonist may be a cyclic dinucleotide (CDN). Exemplary CDNs, including but not limited to cyclic diguanylate monophosphate (c-di-GMP), are described in Nature 2011, DOI: 10.1038/nature10429 and Nat. Chem. Biol. 2014, DOI: 10.1038/nchembio.1661. The STING agonist may be a small molecule agonist.

A payload may be expressed by a target cell from a transgene or mRNA introduced into a extracellular vesicles by electroporation, chemical or polymeric transfection, viral transduction, mechanical membrane disruption, or other method when the target cell is contacted with the extracellular vesicles.

In some instances, the exogenous nucleic acid is an RNA molecule, or a DNA molecule that encodes for an RNA molecule, that silences or represses the expression of a target gene. For example, the molecule can be a small interfering RNA (siRNA), an antisense RNA molecule, or a short hairpin RNA (shRNA) molecule.

Pharmaceutical Compositions and Dosage Forms

Provided herein are pharmaceutical compositions comprising extracellular vesicles that are suitable for administration to a subject. The pharmaceutical compositions generally comprise a plurality of extracellular vesicles and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 18th ed. (1990)). The pharmaceutical compositions are generally formulated sterile and in full compliance with all Good Manufacturing Practice (GMP) regulations of the U.S. Food and Drug Administration.

In some embodiments, the pharmaceutical composition comprises one or more therapeutic agents and the extracellular vesicles described herein. In some embodiments, the extracellular vesicles are co-administered with of one or more separate therapeutic agents, wherein co-administration includes administration of the separate therapeutic agent before, after or concurrent with administration of the extracellular vesicles.

Pharmaceutically-acceptable excipients include excipients that are generally safe (GRAS), non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents may also be incorporated into the compositions. Typically, a pharmaceutical composition is formulated to be compatible with its intended route of administration. The extracellular vesicles can be administered by parenteral, topical, intravenous, oral, subcutaneous, intraarterial, intradermal, transdermal, rectal, intracranial, intraperitoneal, intranasal; intramuscular route or as inhalants. In one embodiment, the pharmaceutical composition comprising extracellular vesicles is administered intravenously, e.g. by injection. The extracellular vesicles can optionally be administered in combination with other therapeutic agents that are at least partly effective in treating the disease, disorder or condition for which the extracellular vesicles are intended.

Solutions or suspensions can include the following components: a sterile diluent such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as manitol, sorbitol, sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the extracellular vesicles in an effective amount and in an appropriate solvent with one or a combination of ingredients enumerated herein, as desired. Generally, dispersions are prepared by incorporating the extracellular vesicles into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The extracellular vesicles can be administered in the form of a depot injection or implant preparation which can be formulated in such a manner to permit a sustained or pulsatile release of the extracellular vesicles.

Systemic administration of compositions comprising extracellular vesicles can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the modified extracellular vesicles are formulated into ointments, salves, gels, or creams as generally known in the art.

EXAMPLES

The invention is further illustrated by the following examples. The examples are provided for illustrative purposes only, and are not to be construed as limiting the scope or content of the invention in any way. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); Green & Sambrook et al., Molecular Cloning: A Laboratory Manual, 4th Edition (Cold Spring Harbor Laboratory Press, 2012); Colowick & Kaplan, Methods In Enzymology (Academic Press); Remington: The Science and Practice of Pharmacy, 22nd Edition (Pharmaceutical Press, 2012); Sundberg & Carey, Advanced Organic Chemistry: Parts A and B, 5th Edition (Springer, 2007).

Example 1: Microfluidization for Loading Exosomes with siRNA

Exosomes were purified chromatographically from a single-use bioreactor (SUB) and formulated in PBS-Sucrose buffer (1.8 mM $KH_2PO_4$, 10 mM $Na_2HPO_4$, 137 mM NaCl, 2.7 mM KCl, 5% w/v sucrose, pH 7.4). Exosomes were mixed with an siRNA targeting kras G12D at a final concentration of 2 μM siRNA and $1 \times 10^{11}$ particles per mL in a 1×PBS, ~1% sucrose buffer. Loading reactions were performed at a 1.0 mL scale, and processed in duplicate over a Microfluidics M110P homogenization module equipped with a F12Y (75 μm) interaction chamber (Microfludics, Westwood, MA). Reactions were held at 20-25° C. by using a heat-exchanger coil configured to the outlet of the interaction chamber submerged in water. Upon processing, samples were filtered using a 0.45 μm PVDF filter and stored at 4° C. Process conditions were screened in a single-pass manner at $1 \times 10^4$, $2 \times 10^4$, and $3 \times 10^4$ psi. Process controls were run in addition to the loading reactions. The entire experimental matrix is shown in Table 1.

TABLE 1

|  | EV only (ctrl) | siRNA only (ctrl) | Process Sample | no Processing (mixing ctrl) |
|---|---|---|---|---|
| 10,000 psi, single pass | | | | |
| SUB-6 UF Pool (3.7E11 p/mL) | 274 uL | 0 uL | 274 uL | 274 uL |
| siRNA (100 μM) | 0 uL | 20 uL | 20 uL | 20 uL |
| 1X PBS, pH 7.4 | 726 uL | 980 uL | 706 uL | 706 uL |
| Total # Samples | 2 | 2 | 2 | 2 |
| 20,000 psi, single pass | | | | |
| SUB-6 UF Pool | 274 uL | 0 uL | 274 uL | 274 uL |
| siRNA | 0 uL | 20 uL | 20 uL | 20 uL |
| 1X PBS, pH 7.4 | 726 uL | 980 uL | 706 uL | 706 uL |
| Total # Samples | 2 | 2 | 2 | 2 |

TABLE 1-continued

|  | EV only (ctrl) | siRNA only (ctrl) | Process Sample | no Processing (mixing ctrl) |
|---|---|---|---|---|
| 30,000 psi, single pass | | | | |
| SUB-6 UF Pool | 274 uL | 0 uL | 274 uL | 274 uL |
| siRNA | 0 uL | 20 uL | 20 uL | 20 uL |
| 1X PBS, pH 7.4 | 726 uL | 980 uL | 706 uL | 706 uL |
| Total # Samples | 2 | 2 | 2 | 2 |

Upon completion of processing, one set of process samples and mixing controls were assayed using nanoparticle tracking analysis (NTA) (Malvern Technologies). The results are shown in Table 2.

TABLE 2

| Sample | p/mL | Mean (nm) | D10 (nm) | D50 (nm) | D90 (nm) |
|---|---|---|---|---|---|
| Mixing Control | 1.11E+11 | 143.8 | 104.8 | 134.4 | 186.0 |
| Process Sample 10,000 psi | 4.39E+10 | 139.9 | 94.3 | 134.7 | 179.0 |
| Process Sample 20,000 psi | 2.57E+10 | 132.4 | 95.1 | 123.1 | 184.7 |
| Process Sample 30,000 psi | 3.36E+10 | 134.9 | 93 | 125.9 | 177.5 |

Through processing, substantial particle loss was observed as a result of sample dilution through the microfluidizer, or as a result of shear-induced homogenization. At this scale of processing, the sample volume was approximately equal to the volumetric holdup of the Microfluidics LV-1 and substantial dilution of the processed sample was expected. Additionally, relative to the mixing control, an approximately 10% reduction in the particle D10 was observed After processing through the microfluidizer, samples were filtered using a 0.45 μm polypropylene filter plate, and added to Panc-1 cells to assay kras knockdown using an mRNA knockdown qPCR assay. The relative kras expression of treated and control cells are shown in FIG. 1. Positive (non-transfected Panc-1 cells) and negative controls (Lipofectamine-transfected Panc-1 with a kras G12D siRNA) were performed in parallel.

The homogenized vesicle samples showed greater knockdown of kras expression as compared to extracellular vesicles (EV), siRNA only, or Mixing control samples. Mixing controls show similar gene expression to the negative control, and reagent only process controls (siRNA only) show normal gene expression. The $3 \times 10^4$ reagent controls showed knockdown when processed independently through the LV-1. When vesicles and siRNA were processed through the LV-1 Microfludizer, a pressure-dependent gene-knockdown effect is observed—with the greatest knockdown seen at a single-pass at the highest concentration of $3 \times 10^4$ psi. These results demonstrate that purified exosomes can be loaded with bioactive payloads and successfully deliver the payload to the cytoplasm of recipient cells.

Example 2: Optimization of Microfluidic Loading Conditions

Figure 2:
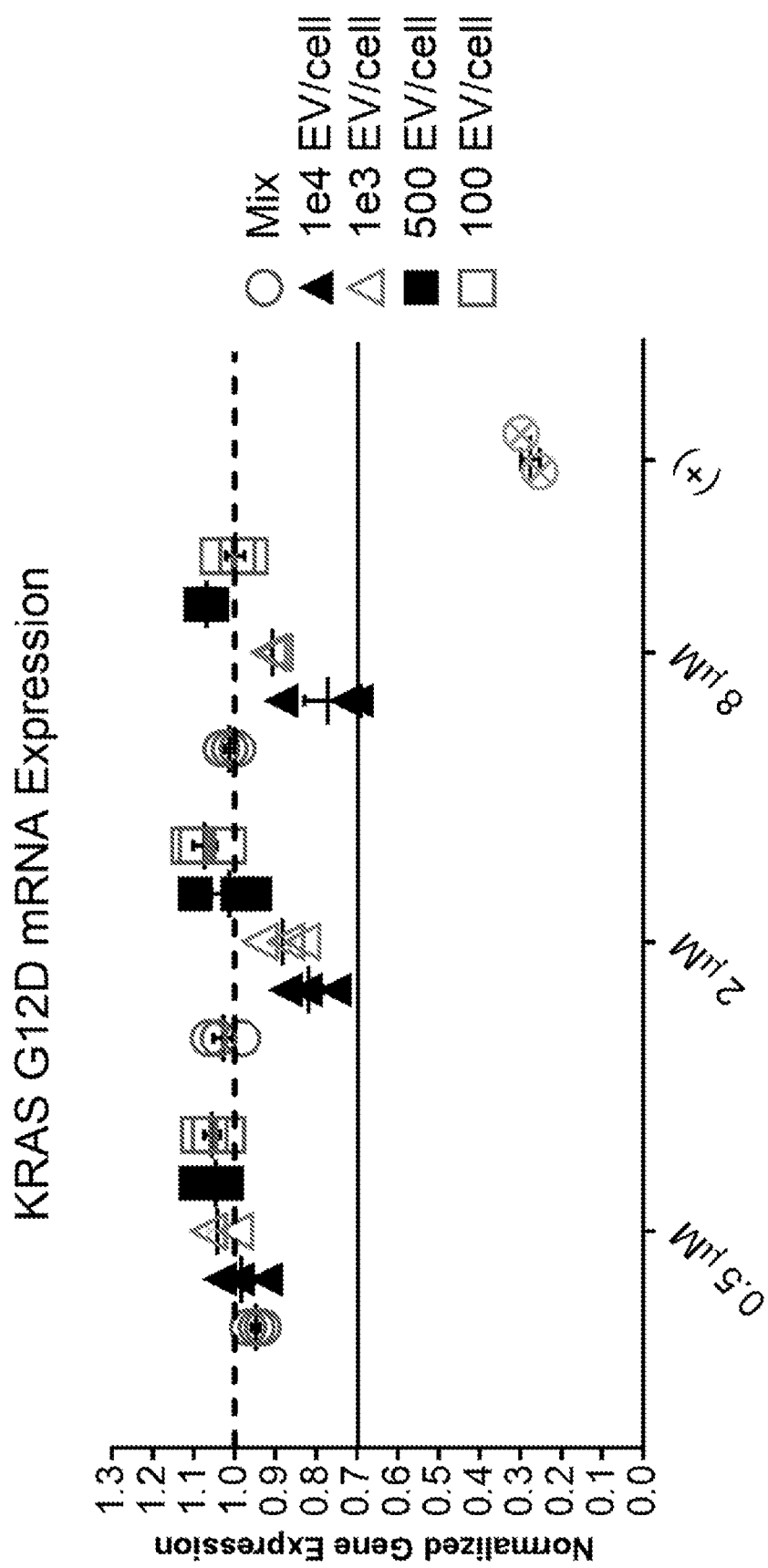
FIG. 2 shows the qPCR results from kras gene knockdown cell based assay in Panc-1 cells as a function of siRNA concentration.

To determine conditions that maximized siRNA loading of exosomes, microfluidic homogenization was carried out as in Example 1 at varying concentrations of siRNA. Exosome samples were processed with kras G12D siRNAs at 0.5 μM, 2 μM, or 8 μM final concentrations. The products from each run were added to cultured Panc-1 cells at concentrations of 100 EV/cell, 500 EV/cell, $1 \times 10^3$ EV/cell or $1 \times 10^4$ EV/cell. As a positive control, Panc-1 cells were transfected with the kras G12D siRNA using Lipofectamine. As shown in FIG. 2, there was a concentration-dependent and dosage-dependent increase in KRAS mRNA knockdown with 8 μM siRNA and $1 \times 10^4$ exosomes resulting in the greatest knockdown.

Another method of loading exosomes with siRNA molecules is to use siRNA duplexes that are covalently fused to a cholesterol moiety. Cholesterol-conjugated siRNAs can associate with the exosome membrane through lipid-lipid interactions between the cholesterol molecule and the phospholipids of the exosome membrane. This loading strategy can increase effective concentration of loaded exosomes and allow for delivery of more siRNA molecules to a recipient cell.

Figure 3:
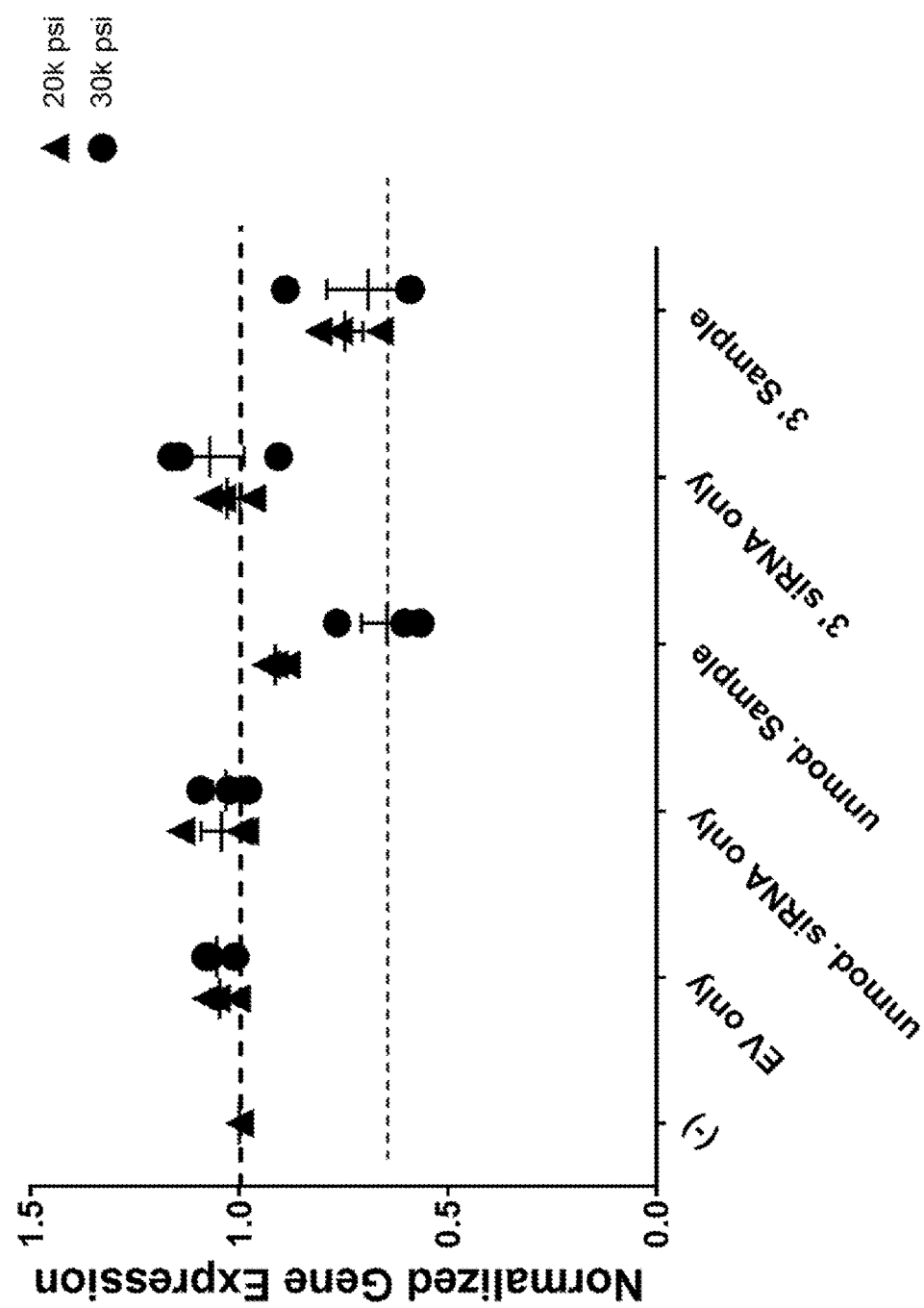
FIG. 3 shows the qPCR results from kras gene knockdown cell based assay in Panc-1 cells using unmodified siRNA and cholesterol-tagged siRNA loaded in exosomes by microfluidic homogenization.

To determine whether microfluidic homogenization can enhance the loading of cholesterol-modified siRNAs, exosomes were loaded as in Example 1 with unmodified kras G12D siRNA or a cholesterol-tagged version of the same miRNA. For controls, these siRNAs were mixed with exosomes without microfluidic homogenization. All samples were processed at either 10,000 psi or 20,000 psi and added to Panc-1 cells at a concentration of $1 \times 10^4$ exosomes per cell. As shown in FIG. 3, at 30,000 psi both the unmodified and cholesterol-tagged siRNAs resulted in significant knockdown of the kras G12D transcript, while none of the mixing controls altered the levels of the transcript. Interestingly, the cholesterol-tagged siRNA could efficiently knock down the transcript at 20,000 psi, while there was very modest knockdown of the transcript at 20,000 psi with the unmodified siRNA. These results demonstrate that microfluidic homogenization can be used for loading lipid-modified siRNAs, and that efficient loading of the siRNAs can be accomplished at relatively low processing pressure.

Figure 4A:
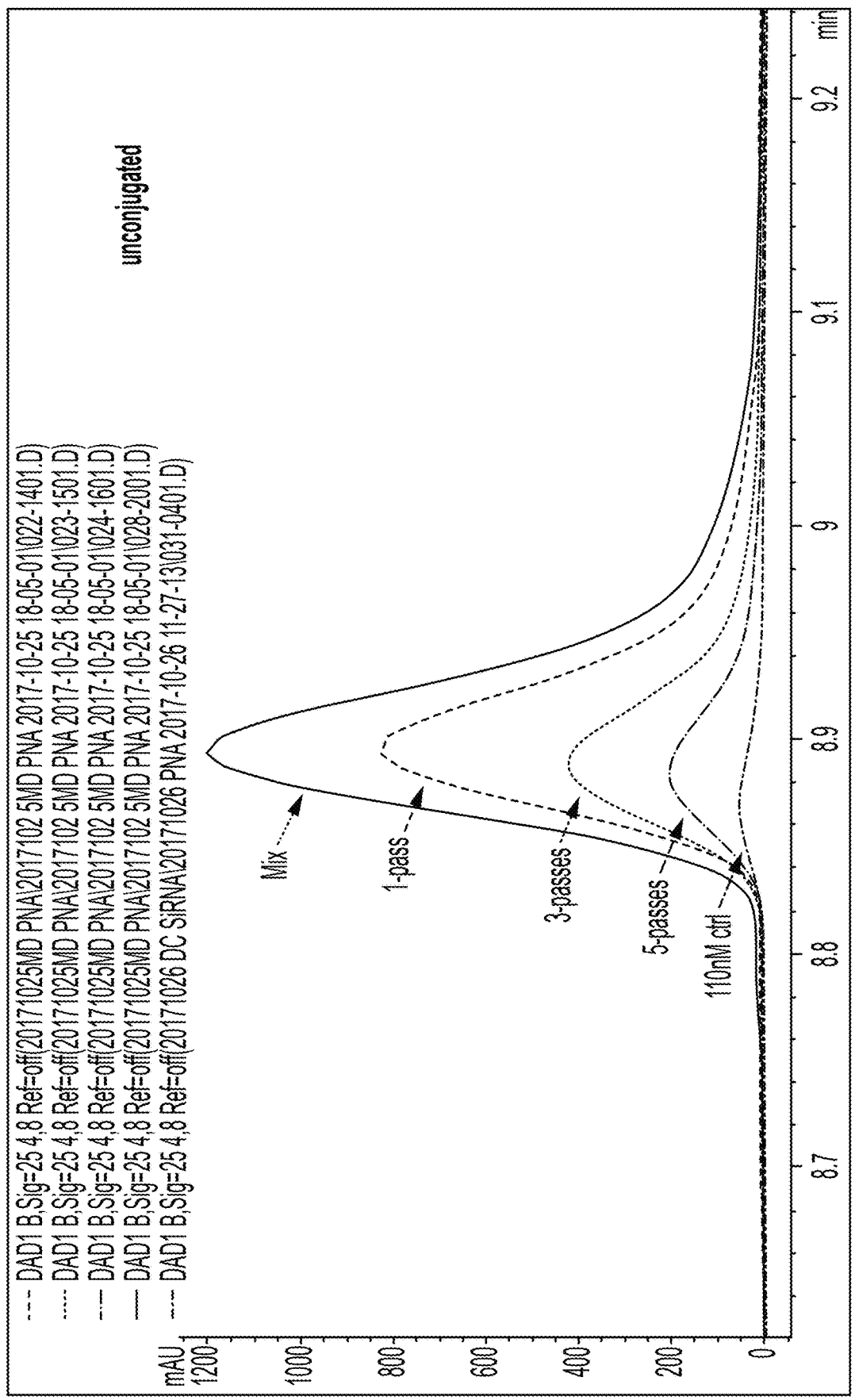

Example 3: Characterization of Exosome and siRNA Integrity After Microfluidization To understand the effects of the forces exerted on siRNAs during microfluidic homogenization, RNA profiles were measured for siRNAs exposed to repeated rounds of homogenization. siRNA (FIG. 4A) or cholesterol-tagged siRNA (FIG. 4B) were processed at 30,000 psi once, three times or five times and analyzed by anion-exchange chromatography with detection at 254 nm. High concentration ("Mix") and low concentration ("110 nM ctrl") control samples that were not processed were used to determine the chromatographic trace of unmodified siRNAs. As shown in FIGS. 4A and 4B, both RNA species were diluted by serial rounds of homogenization, but the shape of the chromatographic trace was not changed, indicating that the structure of the siRNA was resistant to multiple rounds of high-pressure microfluidic processing.

Figure 5B:
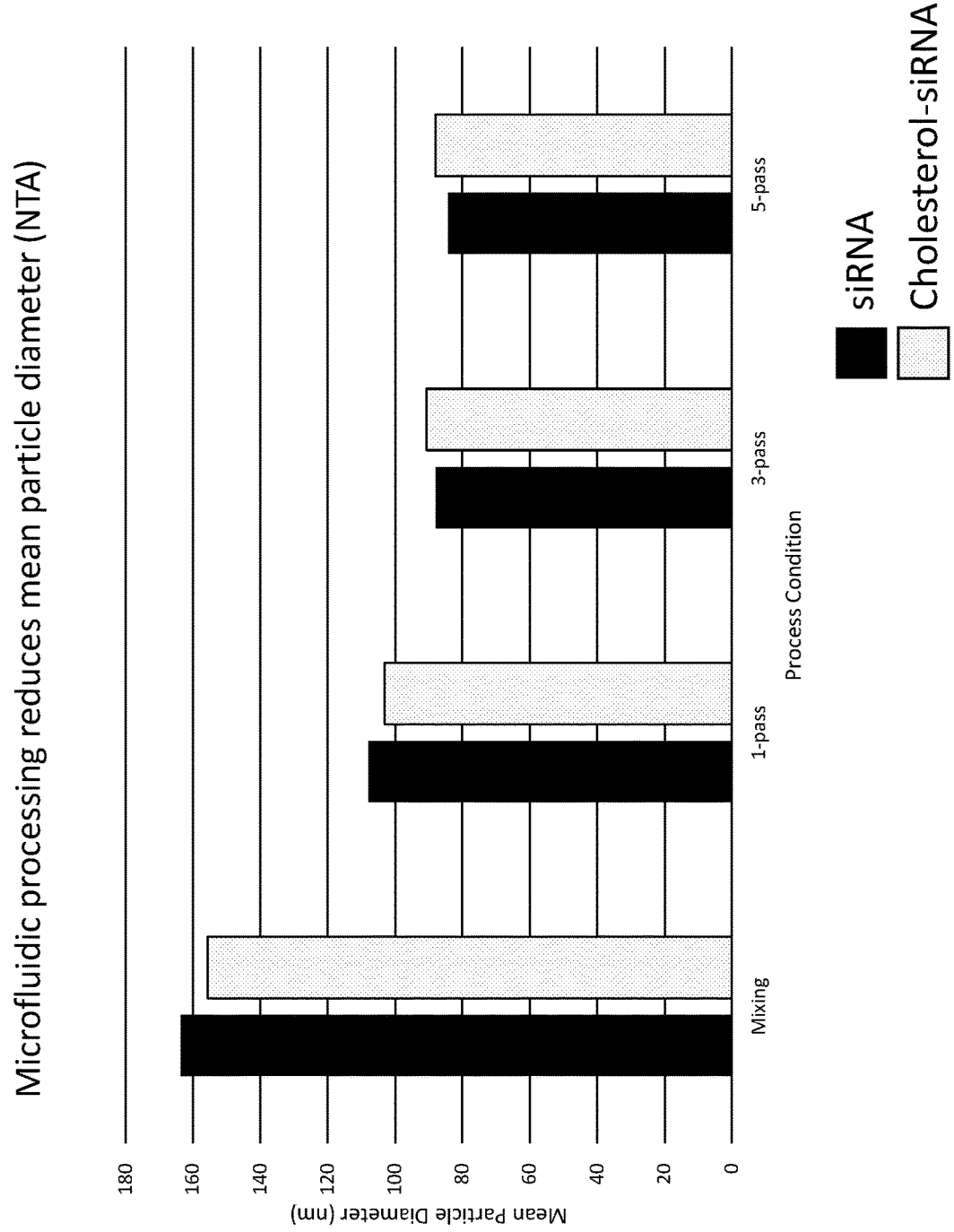

To determine whether the structure of exosomes was altered during repeated rounds of microfluidic homogenization, purified exosome samples were processed once, three times or five times and were analyzed by size exclusion chromatography (SEC) to determine the diameter of the exosome population. As shown in FIGS. 5A and 5B, repeated rounds of homogenization resulted in an increase in retention time ($t_r$), indicating the elution of smaller products (FIG. 5A). This alteration in elution time was validated using NTA, corresponding to a change from ~160 nm average diameter to ~90 nm average diameter (FIG. 5B).

These results demonstrate that repeated microfluidic homogenization of exosomes results in a modest but significant decrease in diameter, perhaps due to shear-mediated fragmentation of the exosomes.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

The present disclosure provides, inter alia, methods of producing exosomes for the delivery of payload molecules. While various specific embodiments have been illustrated and described, the above specification is not restrictive. It will be appreciated that various changes can be made without departing from the spirit and scope of the invention(s). Many variations will become apparent to those skilled in the art upon review of this specification.

The invention claimed is:

1. A method for producing an isolated exosome for delivery of a payload molecule, the method comprising:
modifying an exosome with the payload molecule via homogenization,
isolating the modified exosome containing the payload molecule, and
optionally formulating the isolated modified exosome into a pharmaceutical composition,
wherein the homogenization is microfluidization,
wherein the microfluidization comprises multiple passes,
wherein each of the multiple passes is performed at between 10,000 and 30,000 psi, and
wherein the exosome is in buffered solution and the buffered solution comprises 0.5-5% w/v sucrose.

2. A pharmaceutical composition comprising a plurality of exosomes produced according to the method of claim 1, and a pharmaceutically-acceptable excipient or carrier in a form suitable for administration to a subject.

3. The method of claim 1, wherein the microfluidization comprises three or more passes at between 20,000 and 30,000 psi.

4. The method of claim 1, wherein the microfluidization comprises three or more passes at 30,000 psi.

5. The method of claim 1, wherein the microfluidization comprises a first pass at 10,000 psi and a second pass at 30,000 psi.

6. The method of claim 1, wherein the microfluidization comprises a first pass at 20,000 psi and a second pass at 30,000 psi.

7. The method of claim 1, wherein the microfluidization comprises five or more passes.

8. The method of claim 1, wherein the microfluidization comprises five or more passes at 30,000 psi.

9. The method of claim 1, wherein the payload molecule is siRNA, miRNA, antisense RNA, DNA, a plasmid, mRNA, tRNA, a protein, a carbohydrate, a lipid, a small molecule drug, a toxin, an antibody, a recombinant protein, a viral vector, or a vaccine.

10. The method of claim 9, wherein the payload molecule is siRNA.

11. The method of claim 9, wherein the payload molecule is a modified siRNA or miRNA that is modified to additionally comprise one or more cholesterol molecules.

* * * * *